United States Patent
Zapari et al.

(10) Patent No.: US 11,957,395 B2
(45) Date of Patent: Apr. 16, 2024

(54) ORTHOPEDIC INSTRUMENT ADAPTERS

(71) Applicant: Depuy Synthes Products, Inc., Raynham, MA (US)

(72) Inventors: Fernando Zapari, Fort Wayne, IN (US); Cory Shulaw, Warsaw, IN (US); Aaron Matyas, Fort Wayne, IN (US)

(73) Assignee: DePuy Synthes Products, Inc., Raynham, MA (US)

( * ) Notice: Subject to any disclaimer, the term of this patent is extended or adjusted under 35 U.S.C. 154(b) by 39 days.

(21) Appl. No.: 17/219,041

(22) Filed: Mar. 31, 2021

(65) Prior Publication Data
US 2022/0313336 A1 Oct. 6, 2022

(51) Int. Cl.
*A61B 17/92* (2006.01)

(52) U.S. Cl.
CPC ........ *A61B 17/92* (2013.01); *A61B 2017/925* (2013.01)

(58) Field of Classification Search
CPC ... A61F 2/4603; A61B 17/92; A61B 17/1659; A61B 2017/00477; A61B 2017/00367; F16B 21/076; B65D 2563/103; B65D 2563/107; Y10T 403/595; Y10T 403/608
See application file for complete search history.

(56) References Cited

U.S. PATENT DOCUMENTS

| | | | | |
|---|---|---|---|---|
| 698,721 A * | 4/1902 | Lowe | ........................ | F16B 1/00 403/322.4 |
| 1,021,931 A * | 4/1912 | James | ..................... | B26B 23/00 403/322.4 |
| 1,851,843 A * | 3/1932 | Inman | ................... | E21B 17/046 403/DIG. 4 |
| 2,614,781 A * | 10/1952 | Engel | ..................... | A47B 91/08 279/107 |
| 3,526,040 A * | 9/1970 | Young | ..................... | G01B 3/08 33/809 |

(Continued)

FOREIGN PATENT DOCUMENTS

| | | |
|---|---|---|
| CN | 110996811 A | 4/2020 |
| EP | 2540256 A1 | 1/2013 |

(Continued)

OTHER PUBLICATIONS

Koch, Snap Fit Design. U Penn, Behrend. http://engr.bd.psu.edu/pkoch/plasticdesign/snap_design.htm Available at least Sep. 2, 2003, per Internet Archive. (Year: 2003).*

(Continued)

*Primary Examiner* — David W Bates
(74) *Attorney, Agent, or Firm* — Mintz Levin Cohn Ferris Glovsky (57) ABSTRACT

In general, orthopedic instrument adapters and methods of using orthopedic instrument adapters are provided. In an exemplary embodiment, an adapter is configured to releasably attach to an end effector configured to impact bone. The end effector can be a broach, chisel, or other surgical implement. The adapter includes a spring-loaded hook that is configured to releasably seat in a cut-out formed in the end effector. The adapter is also configured to releasably attach to a surgical impacting tool, such as an orthopedic impactor, configured to drive impacting of the end effector relative to bone.

26 Claims, 7 Drawing Sheets

(56) References Cited

U.S. PATENT DOCUMENTS

| | | | | |
|---|---|---|---|---|
| 3,530,750 | A | * | 9/1970 | Dennis .................. B21D 28/34 83/698.41 |
| 3,600,999 | A | * | 8/1971 | Daniels ................. B21D 28/34 279/90 |
| 3,851,984 | A | * | 12/1974 | Crippa ................. A61C 17/222 473/298 |
| 4,367,971 | A | * | 1/1983 | Coren ................. B25B 23/0035 403/104 |
| 4,392,836 | A | * | 7/1983 | Sugawara ................. G01P 1/04 411/522 |
| 4,826,345 | A | * | 5/1989 | Salice ..................... F16B 12/26 403/231 |
| 4,993,410 | A | * | 2/1991 | Kimsey ................. A61F 2/4607 606/100 |
| 5,089,003 | A | * | 2/1992 | Fallin ................ A61B 17/1668 606/85 |
| 5,531,750 | A | * | 7/1996 | Even-Esh ......... A61B 17/1659 606/85 |
| 5,570,968 | A | * | 11/1996 | Sassmannshausen ...................... F16B 7/1409 248/188.5 |
| 5,664,792 | A | * | 9/1997 | Tseng ..................... B23D 51/10 403/329 |
| 6,174,110 | B1 | * | 1/2001 | Papadopoulos ........... E04G 5/02 405/290 |
| 6,478,503 | B1 | * | 11/2002 | Cheng .................... B62B 9/245 280/47.38 |
| 6,663,636 | B1 | * | 12/2003 | Lin .................... A61B 17/1659 606/85 |
| 7,357,593 | B1 | * | 4/2008 | Florence ................. B25G 3/12 403/321 |
| 8,327,745 | B2 | * | 12/2012 | Lee ...................... B21D 28/34 83/698.91 |
| 8,393,409 | B2 | | 3/2013 | Pedicini |
| 9,027,952 | B2 | * | 5/2015 | Zhu ........................ B62B 7/145 280/30 |
| 9,381,023 | B2 | * | 7/2016 | del Rio ............ A61B 17/32002 |
| 9,687,994 | B2 | * | 6/2017 | Lee ...................... B21D 28/34 |
| D806,493 | S | | 1/2018 | Pomeroy |
| 9,964,377 | B2 | * | 5/2018 | Marvin .................. F41A 29/02 |
| 10,028,754 | B2 | | 7/2018 | Johnson et al. |
| 10,603,050 | B2 | | 3/2020 | Pedicini |
| RE47,963 | E | | 4/2020 | Pedicini |
| 10,624,651 | B2 | | 4/2020 | Aman et al. |
| 2008/0255565 | A1 | * | 10/2008 | Fletcher ............. A61B 17/1668 606/80 |
| 2009/0326540 | A1 | * | 12/2009 | Estes ................ B23B 31/10741 279/78 |
| 2010/0107832 | A1 | * | 5/2010 | Johnston .............. B21D 45/006 83/13 |
| 2011/0236123 | A1 | * | 9/2011 | Melino, Sr. ........... F16B 7/1454 403/81 |
| 2013/0018382 | A1 | * | 1/2013 | Jones .................... A61B 17/92 623/20.35 |
| 2013/0261629 | A1 | * | 10/2013 | Anthony ................ A61B 17/16 606/80 |
| 2013/0261681 | A1 | * | 10/2013 | Bittenson ............... A61B 17/92 606/86 R |
| 2015/0089821 | A1 | * | 4/2015 | Troudt .................... B25G 1/04 16/427 |
| 2018/0028249 | A1 | * | 2/2018 | Jaumard ............... A61F 2/4601 |
| 2018/0055552 | A1 | | 3/2018 | Pedicini |
| 2018/0214281 | A1 | * | 8/2018 | Dykema ................. A61F 2/389 |
| 2018/0338751 | A1 | | 11/2018 | Pedicini |
| 2019/0336307 | A1 | * | 11/2019 | Sungu ................. A61B 17/8872 |
| 2021/0030563 | A1 | * | 2/2021 | Alden .................. A61B 17/921 |
| 2021/0093330 | A1 | | 4/2021 | Tsukayama et al. |
| 2021/0361296 | A1 | * | 11/2021 | Zimmerman ...... A61B 17/1659 |

FOREIGN PATENT DOCUMENTS

| | | |
|---|---|---|
| EP | 2668931 A1 | 12/2013 |
| WO | WO-2018169995 A1 | 9/2018 |
| WO | WO-2019038055 A1 | 2/2019 |

OTHER PUBLICATIONS

SmLease Design, How to Design Snap Fit Joints in Plastic Parts. https://www.smlease.com/entries/plastic-design/how-to-design-snap-fit-joints-in-plastic-parts/ Available at least by Jul. 2020 per earliest comment to the article (found at bottom in weblink). (Year: 2020).*

International Search Report and Written Opinion for Intl. Pat. App. No. PCT/IB2022/05243 dated Jun. 10, 2022 (18 pages).

International Search Report and Written Opinion for Intl. Pat. App. No. PCT/IB2022/052043 dated Jun. 10, 2022 (18 pages).

\* cited by examiner

ORTHOPEDIC INSTRUMENT ADAPTERS

FIELD

The present disclosure generally relates to orthopedic instrument adapters.

BACKGROUND

In the field of orthopedics, prosthetic devices, such as artificial joints, are often implanted or seated in a patient's bone cavity. The cavity is typically formed during surgery before a prosthetic device is seated or implanted by, for example, a physician or other medical professional removing and/or compacting existing bone to form the cavity. The prosthetic device, which can also be referred to as a prosthesis, usually includes a stem or other protrusion that is inserted into the cavity.

To create the cavity, a physician or other medical professional may use a broach, chisel, or other surgical implement conforming to the shape of the stem of the prosthetic device. In general, the surgical implement is impelled into the implant area to form the cavity. One technique for impelling the surgical implement includes a physician or other medical professional manual hammering the surgical impacting tool to impel the surgical implement into the implant area. Another technique for creating the prosthetic cavity relies on computer-controlled robotic arms for creating the cavity instead of using manual power provided by a physician or other medical professional. Another technique for creating the prosthetic cavity is to drive the surgical implement pneumatically, e.g., by compressed air. Another technique for creating the prosthetic cavity relies on a linear compressor to compress air on a single stroke basis and then, after a sufficient pressure is created, to release the air through a valve and onto a striker to impel the surgical implement.

The broach, chisel, or other surgical implement can be removably coupled to the surgical impacting tool to, for example, allow for surgical implements of different sizes and/or shapes to be used with the surgical impacting tool in different surgical procedures to help accommodate a particular patient's needs, to allow for replacement of surgical implements that become worn, damaged, or otherwise undesirable for future use without having to replace a remainder of the surgical impacting tool, and/or to accommodate a surgeon's personal preference of surgical implements. However, various techniques for creating the prosthetic cavity that impel the surgical implement, such as the four techniques discussed above, can loosen the surgical implement's removable coupling to the surgical impacting tool due to the force required to impel the surgical implement. Such loosening may cause the surgical implement to unexpectedly become decoupled from the surgical impacting tool during a surgical procedure, may cause the surgical implement to shake or otherwise move in unintentional direction(s) and thus cause patient harm and/or adversely affect cavity formation, and/or may hinder cavity formation by not allowing the surgical implement to receive and be impelled at full intended force.

Accordingly, there remains a need for improved surgical impacting tools.

SUMMARY

In general, orthopedic instrument adapters and methods of using orthopedic instrument adapters are provided.

In one aspect, a surgical system is provided that in one embodiment includes an end effector and an adapter. The end effector is configured to impact bone. A notch is formed in the end effector. The adaptor includes a rearward end configured to releasably engage an orthopedic impactor, and a spring-loaded lever having a hook at a forward end thereof that is configured to be releasably seated in the notch of the end effector. The hook has a sloped forward surface.

The surgical system can have any number of variations. For example, at least one of horizontal movement of the end effector in a rearward direction and horizontal movement of the adapter in a forward direction can be configured to cause the adapter and the end effector to come into contact, thereby automatically causing movement of the spring-loaded lever such that the hook releasably seats in the notch. In some embodiments, the adapter can also include a release mechanism including a spring, and, with the hook releasably seated in the notch, actuation of the release mechanism can be configured to cause movement of the hook in a vertical direction such that the hook is released from the notch.

For another example, with the notch releasably seating the hook therein, there can be a single point of contact between the hook and the end effector. For yet another example, the hook can have a sloped rearward surface that slopes in a forward direction, and the sloped forward surface can slope in a rearward direction. For still another example, the surgical system can also include one or more additional end effectors, each of the one or more additional end effector can have a notch formed therein, the hook can be configured to releasably seat in one of the notches at a time, and each of the end effector and the one or more additional end effectors can be different from one another.

For yet another example, the surgical system can also include the orthopedic impactor, and, with the adapter releasably engaging the orthopedic impactor and with the hook releasably seated in the notch, the orthopedic impactor can be configured to drive the end effector to repeatedly impact bone. In some embodiments, the orthopedic impactor can be configured to drive the end effector in a horizontal direction, and the hook can be configured to be released from the notch only by moving in a vertical direction.

In another embodiment, a surgical system includes an adaptor including a rearward end configured to releasably engage an orthopedic impactor, a spring, and a lever biased by the spring. The lever has a hook at a forward end thereof that is configured to releasably engage an end effector configured to impact bone. The hook has a sloped forward surface.

The surgical system can vary in any number of ways. For example, the adapter can define a first longitudinal axis extending between the rearward end of the adapter and a forward end of the adapter, and the sloped forward surface can slope at an angle transverse to the first longitudinal axis. In some embodiments, the surgical system can also include the end effector, the end effector can define a second longitudinal axis extending between a rearward end of the end effector and a forward end of the end effector, and the hook can be configured to be released from the end effector only by moving in a direction that is substantially perpendicular to the first longitudinal axis and the second longitudinal axis; and/or the spring can be configured to move between an uncompressed configuration, in which the spring biases the lever downward and the hook is configured to releasably engage the end effector, and a compressed configuration, in which the hook is configured to move in a direction substantially perpendicular to the first longitudinal axis to be released from the end effector.

For another example, the hook can have a sloped rearward surface that slopes in a forward direction, and the sloped forward surface can slope in a rearward direction.

For yet another example, the surgical system can also include the end effector, and a notch can be formed in the end effector and can be configured to releasably seat the hook therein. In some embodiments, with the notch releasably seating the hook therein, there can be a single point of contact between the hook and the end effector.

For still another example, the adapter can also include a release mechanism operably coupled to the spring, and, with the hook releasably engaging the end effector, actuation of the release mechanism can be configured to compress the spring and thereby cause movement of the lever such that the hook is released from the end effector. In some embodiments, the surgical system can also include the end effector, the end effector can define a longitudinal axis extending between a rearward end of the end effector and a forward end of the end effector, and the movement of the lever can be transverse to the longitudinal axis.

For yet another example, the surgical system can also include the end effector, and the end effector can include a broach or a chisel.

For another example, the surgical system can also include the orthopedic impactor, and, with the adapter releasably engaging the orthopedic impactor and with the lever releasably engaging the end effector, the orthopedic impactor can be configured to drive the end effector to repeatedly impact bone.

In another aspect, a surgical method is provided that in one embodiment includes moving at least one of an end effector horizontally in a rearward direction and an adapter in a forward direction such that the adapter and the end effector come into contact, thereby causing movement of a spring-loaded lever of the adapter such that a hook of the lever releasably seats in a notch of the end effector and there is a single point of contact between the lever and the end effector. The surgical method also includes, with the adapter coupled to an orthopedic impactor and with the hook releasably seated in the notch, causing the orthopedic impactor to drive the end effector horizontally to impact bone.

The surgical method can have any number of variations. For example, the hook can have a sloped forward surface and a sloped rearward surface. For another example, the hook can only be releasable from the notch by moving vertically relative to the end effector.

For yet another example, the surgical method can also include actuating a release mechanism of the adapter, thereby causing the hook to be released from the notch. In some embodiments, the actuation of the release mechanism can cause the hook to move vertically to be released from the notch; and/or a spring of the actuator can decompress in response to the hook being seated in the notch, and the actuation of the release mechanism can cause the spring to compress.

For still another example, the end effector can include a broach or a chisel.

BRIEF DESCRIPTION OF DRAWINGS

This disclosure will be more fully understood from the following detailed description taken in conjunction with the accompanying drawings, in which.

DETAILED DESCRIPTION

Certain exemplary embodiments will now be described to provide an overall understanding of the principles of the structure, function, manufacture, and use of the devices and methods disclosed herein. One or more examples of these embodiments are illustrated in the accompanying drawings. Those skilled in the art will understand that the devices, systems, and methods specifically described herein and illustrated in the accompanying drawings are non-limiting exemplary embodiments and that the scope of the present invention is defined solely by the claims. The features illustrated or described in connection with one exemplary embodiment may be combined with the features of other embodiments. Such modifications and variations are intended to be included within the scope of the present invention.

Further, in the present disclosure, like-named components of the embodiments generally have similar features, and thus within a particular embodiment each feature of each like-named component is not necessarily fully elaborated upon. Additionally, to the extent that linear or circular dimensions are used in the description of the disclosed systems, devices, and methods, such dimensions are not intended to limit the types of shapes that can be used in conjunction with such systems, devices, and methods. A person skilled in the art will recognize that an equivalent to such linear and circular dimensions can easily be determined for any geometric shape. Sizes and shapes of the systems and devices, and the components thereof, can depend at least on the anatomy of the subject in which the systems and devices will be used, the size and shape of components with which the systems and devices will be used, and the methods and procedures in which the systems and devices will be used.

In general, orthopedic instrument adapters and methods of using orthopedic instrument adapters are provided. In an exemplary embodiment, an adapter is configured to releasably attach to an end effector configured to impact bone. The end effector can be a broach, chisel, or other surgical implement. The adapter includes a spring-loaded hook that is configured to releasably seat in a cut-out formed in the end effector. The hook being spring-loaded may allow the hook to be quickly and automatically seated in the end effector's cut-out when the hook is moved into contact with the end effector and/or the end effector is moved into contact with the hook. A user, e.g., a surgeon or other medical professional, thus does not need to take any particular action to attach the adapter and the end effector together other than simply moving the two components into contact with one another. De-coupling of the adapter and end effector may also be quickly and simply achieved by compressing the adapter's spring, such as by pressing a button of the adapter or actuating another actuator of the adapter, to release the hook from the cut-out.

The adapter is also configured to releasably attach to a surgical impacting tool, such as an orthopedic impactor, configured to drive impacting of the end effector relative to bone. The adapter being releasably attachable to the surgical impacting tool allows the adapter to be releasably attachable to a variety of different surgical impacting tools to allow the different surgical impacting tools to each be used with a variety of different end effectors each releasably attachable to the adapter. Each of the end effectors can be different from one another in shape and/or size, thereby allowing for a particular end effector to be selected by a surgeon (or other medical professional) for optimal desired impacting in a particular surgical procedure being performed on a particular patient's bone. In some embodiments, instead of being releasably attachable to the surgical impacting tool, the adapter can be non-releasably attached to the surgical impacting tool to allow the surgical impacting tool to be used with a variety of different end effectors.

A rearward end of the adapter is configured to releasably attach to the surgical impacting tool, and a forward end of the adapter is configured to releasably attach to the end effector. The hook has a chamfered forward surface that slopes in a rearward direction toward a tip of the hook. The tip of the hook defines a single point of contact between the hook and the end effector when the adapter is releasably attached to the end effector. The surgical impacting tool releasably attached to the adapter is configured to provide a horizontally directed force to the end effector, via the adapter, to drive the impacting of the end effector. The hook is configured to move vertically into the cut-out to attach the adapter to the end effector and to move vertically out of the cut-out to release the adapter from the end effector. The single point of contact between the hook and the end effector may help maintain secure attachment of the adapter and the end effector during impacting since the horizontally directed force from the surgical impacting tool will not urge vertical movement of the adapter or the end effector.

FIGS. 1-4 illustrate one embodiment of an adapter 100 configured to releasably attach to an end effector configured to impact bone. The adapter 100 includes a body 102, a lever 104, a pin 106 that pivotally attaches the lever 104 to the body 102, and a spring 108 that facilitates movement of the lever 104 relative to the body 102. The lever 104 includes a hook 110 and a button 112. The hook 110 is configured to releasably seat in a notch (also referred to herein as a "cut-out") formed in the end effector to releasably attach the adapter 100 and the end effector. The button 112 is configured to facilitate seating of the hook 110 in and release of the hook 110 from the notch.

The pin 106 defines a pivot point about which the lever 104 is configured to pivot relative to the body 102. The lever 104 includes a passageway 114 formed therethrough configured to seat the pin 106 therein. The body 102 has opposed channels 116 formed through left and right sidewalls of the body 102 that are configured to seat the pin 106 therein. The pin 106 is seated in the passageway 114 and in the channels 116 in FIGS. 1, 3, and 4. As in this illustrated embodiment, the pin 106 can be fixed in position relative to the body 102 and the lever 104, which may help facilitate smooth pivoting of the lever 104 about the pin 106 relative to the body 102. The pin 106 can be fixed in the passageway 114 and the channels 116 in any of a variety of ways, such as by being seated therein via interference fit, using adhesive, via welding, etc.

The pin 106 is a single solid cylindrical rod in this illustrated embodiment. In other embodiments the pin 106 can have another configuration. For example, the pin 106 can be a single hollow cylindrical rod. The pin 106 being a single cylindrical rod (hollow or solid) may help facilitate smooth pivotal motion of the lever 104 relative to the body 102 by extending through an entire width of the lever 104. For another example, the pin 106 can include a first cylindrical rod (hollow or solid) that attaches to a left or right side of the body 102 and the lever 104 and a second cylindrical rod (hollow or solid) that attaches to the other of the left and right sides of the body 102 and the lever 104. The pin 106 including two pivot pins may facilitate manufacturing of the adapter 100, e.g., because the passageway 114 does not need to be formed in the lever 104 to receive a single pin therethrough. For yet another example, the pin 106 can be integrally formed with the lever 104 and configured to be seated in the body 102. For still another example, the pin 106 can be integrally formed with the body 102 and configured to be seated in the lever 104.

Figure 1:
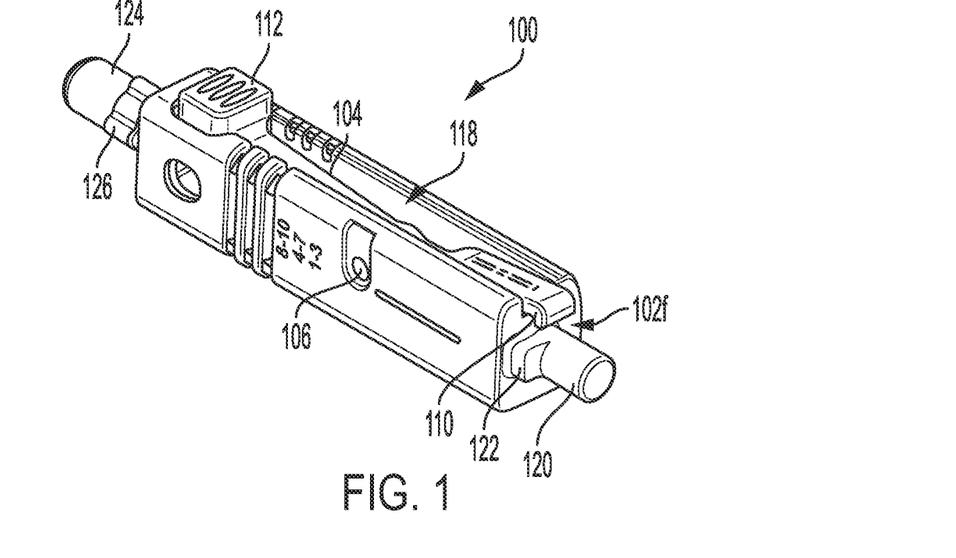
FIG. 1 is a perspective view of one embodiment of an adapter.
Figure 2:
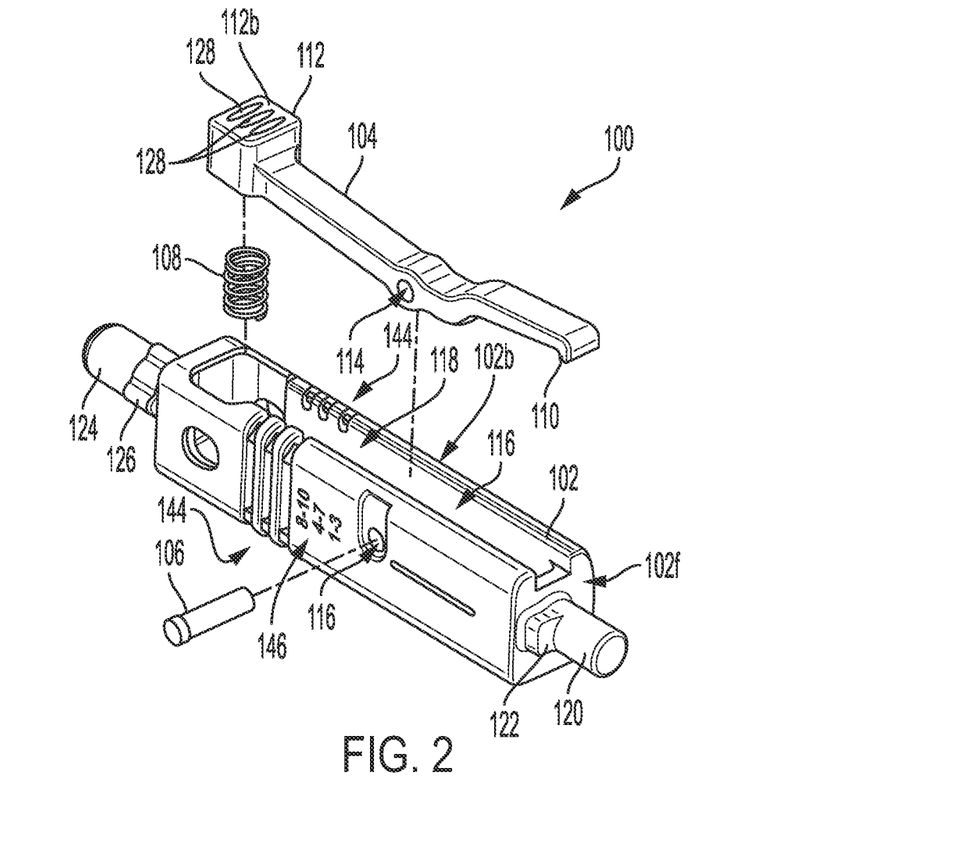
FIG. 2 is an exploded view of the adapter of FIG. 1.
Figure 3:
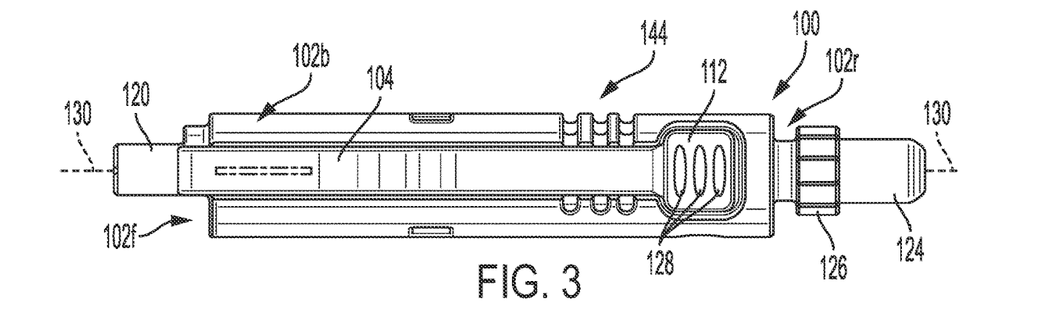
FIG. 3 is a bottom view of the adapter of FIG. 1.
Figure 4:
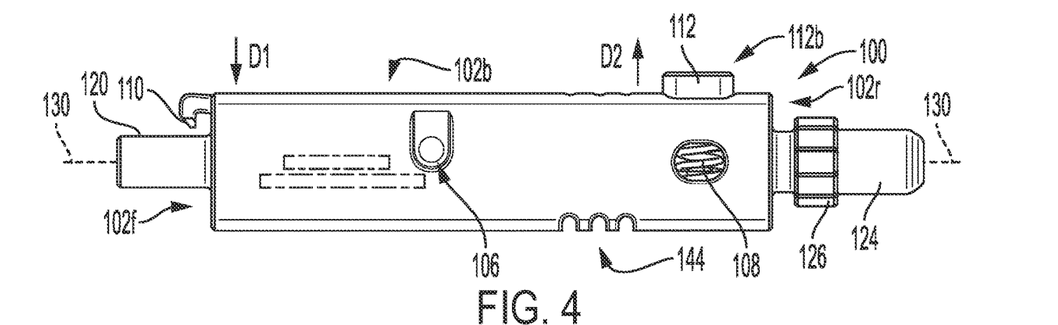
FIG. 4 is a side view of the adapter of FIG. 1.

The body 102 has a cavity 118 formed therein. The cavity 118 is configured to seat the spring 108 and the lever 104 therein, as shown in FIGS. 1, 3, and 4. A size and shape of the cavity 118 generally depends on a size and shape of each of the spring 108 and the lever 104. The cavity 118 is configured to fully seat the spring 108 therein, as shown in FIGS. 1, 3, and 4. The cavity 118 is configured to partially seat the lever 104 therein, as also shown in FIGS. 1, 3, and 4. At least the button 112 and the hook 110 of the lever 104 are configured to be located outside the body 102 and thus at least partially be located outside of the cavity 118. As shown in FIGS. 1 and 4, the button 112 extends beyond a bottom-facing surface 102b of the body 102, which may facilitate user access of the button 112 for manually pressing by the user, as discussed further below. As shown in FIGS. 1, 3, and 4, the hook 110 extends beyond a forward-facing surface 102f of the body 102, which may allow the hook 110 to hook into a notch formed in an end effector, as discussed further below. In an exemplary embodiment, with the hook 110 seated in the notch, the forward-facing surface 102f of the body 102 abuts against a rearward-facing surface of the end effector, which may help stabilize the adapter 100 relative to the end effector.

The adapter 100 includes a stabilizer 120 at a forward end of the body 102. The stabilizer 120 extends forwardly from the body 102. The stabilizer 120 is configured to be releasably seated in a cavity formed in an end effector having a notch formed therein in which the hook 110 is configured to be seated. The stabilizer 120 is configured to releasably engage the end effector to help stabilize the adapter 100 relative to the end effector. A size and shape of the stabilizer 120 generally depends on a size and shape of an end effector to which the adapter 100 is configured to releasably attach.

As in this illustrated embodiment, the stabilizer 120 can include a key element 122 configured to seat in a corresponding key feature of the end effector adjacent to the end effector's cavity. The key element 122 is configured to seat within the key feature of the end effector to help ensure that the adapter 100 is at a predetermined rotational alignment with the end effector. A size and shape of key element 122 generally depends on a size and shape of an end effector to which the adapter 100 is configured to releasably attach. If the key element 122 is not seated in the end effector's key feature, the body's forward-facing surface 102f cannot abut the end effector's rearward-facing surface, thereby indicating that the adapter 100 has not been properly attached to the end effector.

The adapter 100 in this illustrated embodiment is configured to releasably attach to a surgical impacting tool, such as an orthopedic impactor, configured to drive impacting of the end effector that is releasably attached to the adapter 100. The adapter 100 includes a connector 124 at a rearward end of the body 102 that is configured to releasably attach to a surgical impacting tool. The connector 124 extends rearwardly from the body 102. A size and shape of connector 124 generally depends on a size and shape of a surgical impacting tool to which the adapter 100 is configured to releasably attach. As mentioned above, in other embodiments, the adapter 100 can be non-releasably attached to a surgical impacting tool. In such embodiments, the connector 124 can be omitted from the adapter 100.

As in this illustrated embodiment, the connector 124 can include a key element 126 configured to be received in a corresponding key feature of a surgical impacting tool. The key element 126 is configured to be received within the key feature of the surgical impacting tool to help ensure that the adapter 100 is at a predetermined rotational alignment with the surgical impacting tool. A size and shape of key element 126 generally depends on a size and shape of a surgical impacting tool to which the adapter 100 is configured to releasably attach. If the key element 126 is not received by the surgical impacting tool's key feature, a rearward-facing surface 102r of the body 102 cannot abut a forward-facing surface of the surgical impacting tool, thereby indicating that the adapter 100 has not been properly attached to the surgical impacting tool.

The button 112 is configured to be actuated by a user to cause movement of the hook 110 and thus of the lever 104. As discussed further below, the movement of the hook 110 facilitates attachment of the adapter 100 to an end effector and release of the adapter 100 from the end effector after the adapter's attachment thereto. The button 112 has a square cube shape in this illustrated embodiment but can have other shapes such as spherical, hemispherical, rectangular box, etc.

As in this illustrated embodiment, the button 112 includes a gripping feature 128 configured to facilitate a user's finger grip of the button 112. The gripping feature 128 in this illustrated embodiment includes a plurality of depressions formed in a bottom-facing surface 112b of the button 112 but can have another configuration, such as a plurality of protrusions extending from the button 112, a textured surface, rubber or other material configured to provide friction, etc. The gripping feature 128 being on the bottom-facing surface 112b of the button 112 reflects a typical hand position on the adapter 100 with the adapter 100 releasably coupled to an end effector. In this typical hand position, a user's thumb can rest on the bottom-facing surface 112b of the button 112.

The spring 108 is configured to provide a bias force to the lever 104. The spring 108 is configured to bias the hook 110 of the lever 104 in a first direction D1 and to bias the button 112 of the lever 104 in a second direction D2 that is opposite to the first direction D1. The first direction D1 is a direction toward the body's cavity 118, which is a direction toward a top side of the adapter 100 since the cavity 118 is formed in a bottom side of the body 102. The force provided to the hook 110 by the spring 108 urges the hook 110 into a notch of an end effector. The force provided to the button 112 by the spring 108 urges the button 112 away from the body 102 of the adapter 100 to help keep the button 112 accessible to a user of the adapter 100. As shown in FIG. 4, the first and second directions D1, D2 are vertical directions. A horizontal direction is defined by a longitudinal axis 130 of the adapter 100 that extends rearward/forward.

The spring 108 is a coil spring in this illustrated embodiment but can be another bias element, such as another type of spring (e.g., a torsion spring, a compression spring, etc.), an elastic cable, etc. The spring 108 is a single bias element in this illustrated embodiment but can in other embodiments include a plurality of bias elements.

The spring 108 is disposed in the cavity 118 of the body 102 and is aligned with the button 112 of the lever 104. The location of the spring 108 relative to the lever 104 is such that actuating the button 112, e.g., pressing of the button 112 in the second direction D2, is configured to cause movement of the spring 108. The spring 108 is configured to move between an uncompressed configuration and a compressed configuration. The spring 108 is biased to the uncompressed configuration. In the uncompressed configuration, the spring 108 provides the bias force to the lever 104 so as to urge the hook 110 in the first direction D1 and the button 112 in the second direction D2. Actuation of the button 112 is configured to press on the spring 108. The button 112 being actuated is configured to move the spring 108 from the uncompressed configuration to the compressed configuration and to pivot the lever 104 at the pivot point defined by the pin 106. The button 112 thus moves in the first direction D1, and the hook 110 moves in the second direction D2. Releasing the button 112 is configured to allow the spring 108 to move from the compressed configuration to the uncompressed configuration such that the lever 104 pivots at the pivot point so as to move the hook 110 in the first direction D1 and move the button 112 in the second direction D2.

Figure 5:
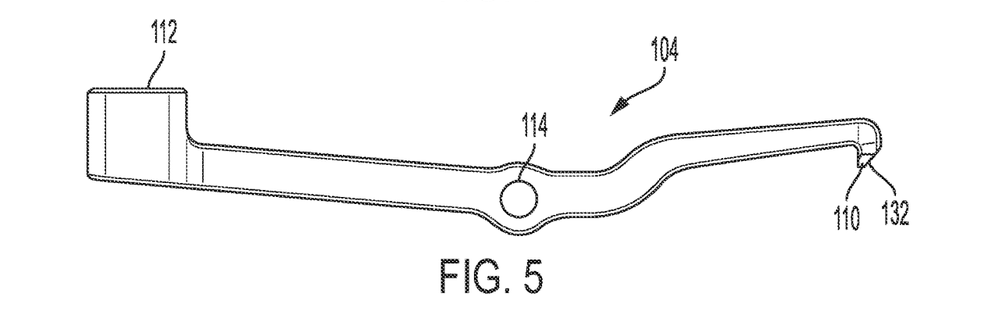
FIG. 5 is a side view of a lever of the adapter of FIG. 1.
Figure 6:
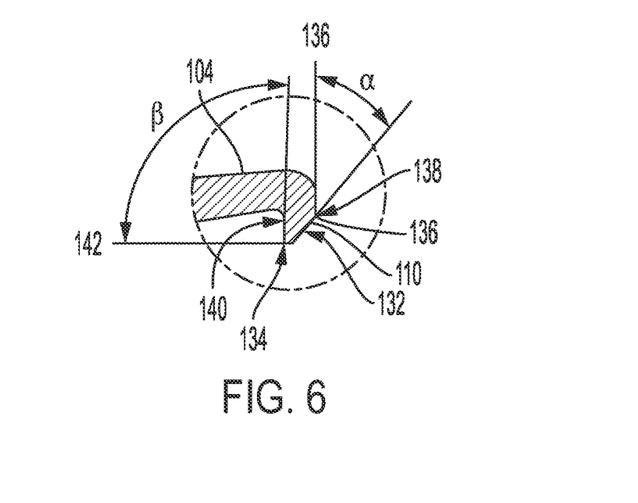
FIG. 6 is a side cross-sectional view of a portion of the lever of FIG. 5.

The lever 104 includes the hook 110 at a forward end of the lever 104 and includes the button 112 at a rearward end of the lever 104. FIGS. 1-4 illustrate the lever 104 as part of the adapter 100, FIG. 5 illustrates the lever 104 as a standalone element, and FIG. 6 illustrates a forward portion of the lever 104.

The hook 110 has a forward surface 132 that slopes in a rearward direction toward a tip 134 of the hook 110. The forward surface 132 slopes at an angle α with respect to a vertical axis 136 defined by a vertical forward surface 138 of the hook 110. The sloped forward surface 132 is configured to facilitate contact of the hook 110 and an end effector at a single point of contact, as discussed further below. The sloped forward surface 132 is also configured to engage a corresponding sloped surface of an end effector during attachment of the adapter 100 to the end effector to facilitate the adapter's attachment to the end effector, as discussed further below. The angle α is about 40° in this illustrated embodiment, but another angle α is possible. A person skilled in the art will appreciate that a value may not be precisely at a value but nevertheless considered to be about that value due to any of a variety of factors, such as manufacturing tolerances and sensitivity of measurement equipment.

The hook 110 has a rearward surface 140 that slopes in a forward direction. The rearward surface 140 slopes at an angle β relative to a horizontal axis 142 extending tangent to the hook tip 134. In an exemplary embodiment, the angle β is greater than 90°, e.g., greater than 90° and less than 135°, greater than 90° and less than 120°, greater than 90° and less than 100°, greater than 90° and less than 95°, greater than 90° and less than 93°, etc. The angle β is about 92° in this illustrated embodiment, but another angle β is possible. The angle β being greater than 90° is configured to prevent non-normal forces between the adapter and a surgical impacting tool to which the adapter 100 is releasably attached, which may help prevent the adapter 100 from accidentally detaching from the surgical impacting tool during impacting, in which the surgical impacting tool provides a horizontally directed force. The angle β being greater than 90° may also allow for clearance between the hook 110 and a surface of a notch in which the hook 110 is seated, as discussed further below.

Figure 7:
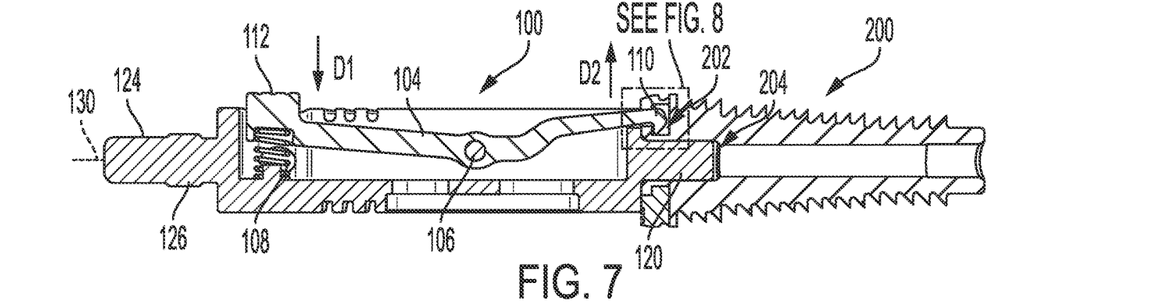
FIG. 7 is a cross-sectional view of the adapter of FIG. 1 coupled to one embodiment of an end effector.
Figure 8:
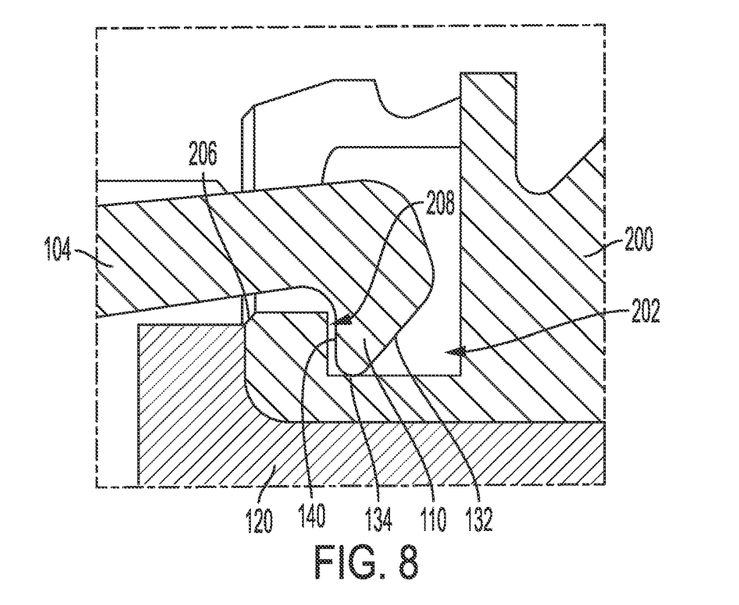
FIG. 8 is an enlarged view of a portion of FIG. 7.

FIG. 7 illustrates the adapter 100 releasably attached to one embodiment of an end effector 200. The end effector 200 is a broach (in particular a femoral broach) in this illustrated embodiment, but as mentioned above, the adapter 100 can be releasably attachable to other types of end effectors. As shown in FIGS. 7 and 8, the end effector 200 includes a notch 202 formed therein in which the hook 110 is seated. The end effector 200 also includes a cavity 204 formed therein at a rearward end thereof that seats the stabilizer 120 of the adapter 100. As shown in FIGS. 7 and 8, with the hook 110 seated in the notch 202 and the stabilizer 120 seated in the cavity 204, the forward-facing surface 102f of the body 102 abuts a rearward-facing surface of the end effector 200, thereby indicating that the adapter 100 has been properly attached to the end effector 200. Although obscured in FIGS. 7 and 8, the key element 122 of the adapter 100 is seated in a key feature of the end effector 200.

With the hook 110 seated in the notch 202, the tip of the hook 134 defines a single point of contact between the hook 110 and the end effector 200, as shown in FIG. 8. The single point of contact is such that the hook 110 and the end effector 200 are above/below one another in a vertical direction. As discussed herein, the single point of contact between the hook 110 and the end effector 200 may help maintain secure attachment of the adapter 100 and the end effector 200 during impacting since a horizontally directed force from the surgical impacting tool to drive the end effector's impacting of bone will not urge vertical movement of the adapter 100 or the end effector 200. The rearward surface 140 of the hook 110 being sloped provides clearance of the hook 110 from a forward surface 208 of the notch 202 so as to facilitate the hook 110 having a single point of the contact with the notch 202.

In an exemplary embodiment, the adapter 100 is releasably attached to the end effector 200 by the end effector 200 moving horizontally in a rearward direction toward the adapter 100 and/or the adapter 100 moving horizontally in a forward direction toward the end effector 200. The adapter 100 and the end effector 200 coming into contact automatically causes movement of the lever 104, e.g., pivoting of the lever 104 at the pivot point, such that the hook 110 releasably seats in the notch 202. The stabilizer 120 will slide horizontally into the end effector's cavity 204 when the adapter 100 and/or the end effector 200 is moved horizontally. The horizontal movement of the adapter 100 and/or the end effector 200 will cause the forward surface 132 of the hook 100 to come into contact with a rearward surface 206 of the end effector 200. The end effector's rearward surface 206 slopes in a forward direction at an angle that corresponds to the angle α of the hook's forward surface 132. The engagement of the hook's forward surface 132 and the end effector's rearward surface 206 will urge the hook 110 to move vertically in the second direction D2. Consequently, the spring 108 will compress and the button 112 will move vertically in the first direction D1. When the tip 134 of the hook 110 clears the end effector's rearward surface 206, the spring's bias force will cause the hook 110 to move vertically in the first direction D1, which is a direction into the notch 202. Consequently, the spring 108 will decompress and the button 112 will move vertically in the second direction D2. The bias force provided by the spring 108 to the lever 104 will continuously urge the hook 110 into the notch 202 until the button 112 is actuated. The actuation of the button 112 will, as discussed above, cause the hook 110 to move vertically in the second direction D2, thereby allowing the end effector 200 to move horizontally in the forward direction away from the adapter 100 and/or the adapter 100 to move horizontally in the rearward direction away from the end effector 200 to release the adapter 100 from the end effector 200. The stabilizer 120 will slide horizontally out of the end effector's cavity 204 when the adapter 100 and/or the end effector 200 is moved horizontally to release the adapter 100 from the end effector 200.

In some embodiments, the button 112 is not actuated during attachment of the adapter 100 and the end effector 200 so the hook 110 can seat automatically in the end effector's notch as discussed herein with the hook's forward surface 132 sliding along the end effector's rearward surface 206. In other embodiments, the button 112 is actuated during attachment of the adapter 100 and the end effector 200. In such embodiments, the body's forward-facing surface 102f abutting the end effector's rearward-facing surface indicates that the hook 110 is properly aligned with the notch 202 and thus that the button 112 can be released to move the hook 110 into the notch 202.

With the adapter 100 and the end effector 200 releasably attached together, the adapter 100 can be releasably attached to a surgical impacting tool as discussed herein. Alternatively, the adapter 100 can be releasably attached to a surgical impacting tool before being releasably attached to the end effector 200.

Figure 9:
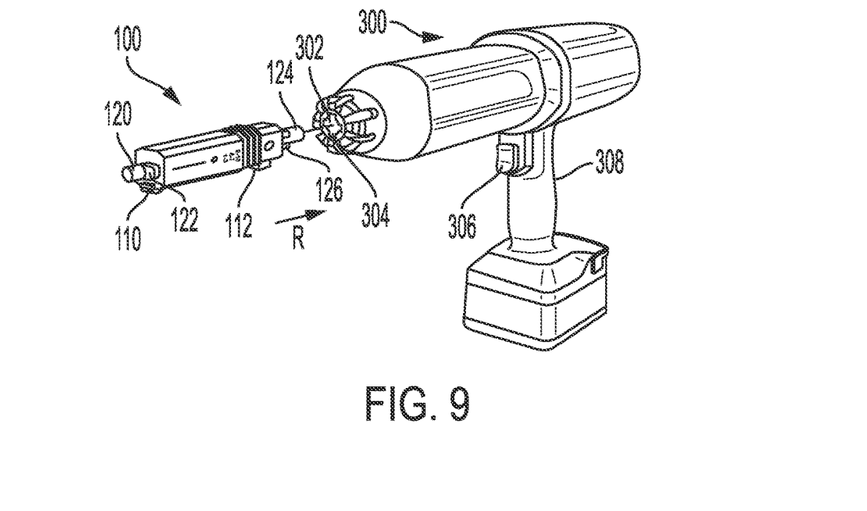
FIG. 9 is a perspective view of the adapter of FIG. 1 and one embodiment of a surgical impacting tool.

FIG. 9 illustrates the adapter 100 being releasably attached to one embodiment of a surgical impacting tool 300. The surgical impacting tool 300 is an orthopedic impactor in this illustrated embodiment, but as mentioned above, the adapter 100 can be releasably attachable to other types of surgical impacting tools.

The surgical impacting tool 300 includes a cavity 302 at a forward end thereof that is configured to receive the connector 124 of the adapter 100 therein. The surgical impacting tool 300 also includes a key feature 304 configured to receive therein the key element 126 of the adapter 100. The key feature 304 and the key element 126 each include a plurality of corresponding spokes extending radially outward. Each of the key feature's radial spokes is configured to receive therein one of the key element's radial spokes. If the key element's radial spokes are not properly aligned with the key feature's radial spokes, the connector 124 cannot be positioned within the cavity 302 of the surgical impacting tool 300 and the rearward-facing surface 102r of the body 102 cannot abut a forward-facing surface of the surgical impacting tool 300. At least one of the radial spokes of each of the key feature 304 and the key element 126 can have a different size and/or shape than the other radial spokes such that the adapter 100 can only be releasably attached to the surgical impacting tool 300 at one rotational position relative to the surgical impacting tool 300. The adapter 100 can thus be in a predictable orientation relative to the surgical impacting tool 300 during impacting.

In an exemplary embodiment, the adapter 100 is releasably attached to the surgical impacting tool 300 by the surgical impacting tool 300 moving horizontally in a forward direction toward the adapter 100 and/or the adapter 100 moving horizontally in a rearward direction toward the surgical impacting tool 300. FIG. 9 shows the adapter 100 moving horizontally in a rearward direction (arrow R) toward the surgical impacting tool 300 to attach to the surgical impacting tool 300.

Figure 10:
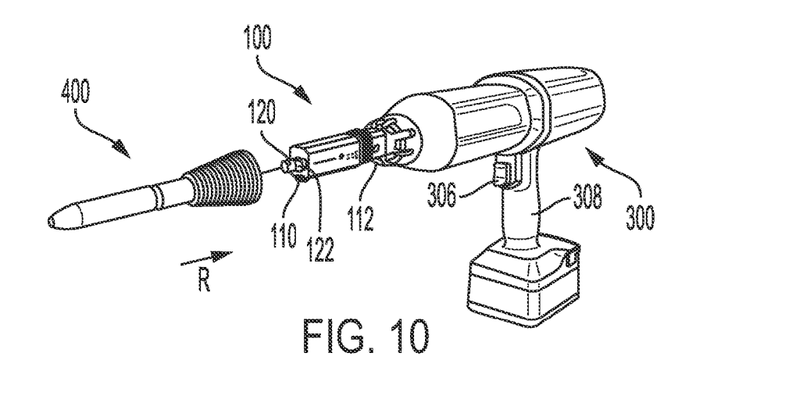
FIG. 10 is a perspective view of the adapter and the surgical impacting tool of FIG. 9 coupled together and of another embodiment of an end effector.

FIG. 10 shows the adapter 100 releasably attached to the surgical impacting tool 300. The connector 124 is seated in the cavity 302, and the rearward-facing surface 102r of the body 102 abuts the forward-facing surface of the surgical impacting tool 300.

FIG. 10 also shows the adapter 100 (attached to the surgical impacting tool 300) being attached to another embodiment of an end effector 400. The end effector 400 is a broach (in particular a tibial broach) in this illustrated embodiment, but as mentioned above, the adapter 100 can be releasably attachable to other types of end effectors. As also mentioned above, the adapter 100 can be releasably attached to the end effector 400 before being releasably attached to the surgical impacting tool 300. The end effector 400 includes a notch 404 (see FIG. 13) configured to seat the hook 110 therein, similar to that discussed above regarding the notch 202 of the end effector 200 seating the hook 110 therein. The end effector 400 also includes a cavity 406 (see FIG. 13) configured to seat the stabilizer 120 therein, similar to that discussed above regarding the cavity 204 of the end effector 200. The end effector 400 also includes a key feature 408 (see FIG. 13) configured to receive the key element 122 of the adapter 100, similar to that discussed above. The adapter 100 is being attached to the end effector 400 in this illustrated embodiment with the end effector 400 being moved horizontally in the rearward direction (arrow R) toward the adapter 100, but as mentioned above, the adapter 100 can alternatively or additionally be moved horizontally in the forward direction toward the end effector 400. As mentioned above with respect to the end effector 200, the button 112 may or may not be actuated during attachment of the adapter 100 to the end effector 400.

Figure 11:
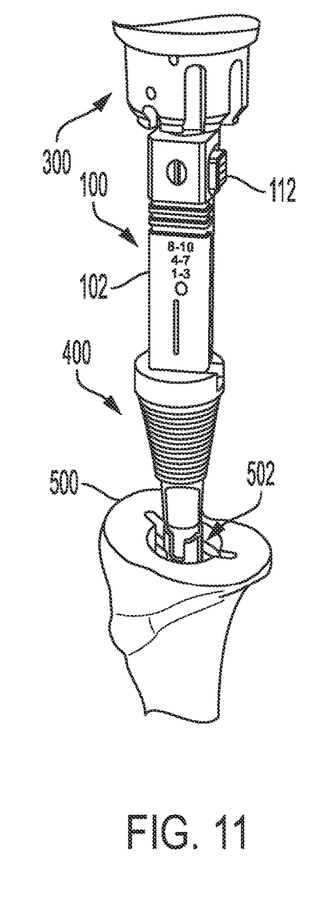
FIG. 11 is a perspective view of the adapter, the surgical impacting tool, and the end effector of FIG. 10 coupled together and with a portion of the end effector positioned in a tibia.
Figure 12:
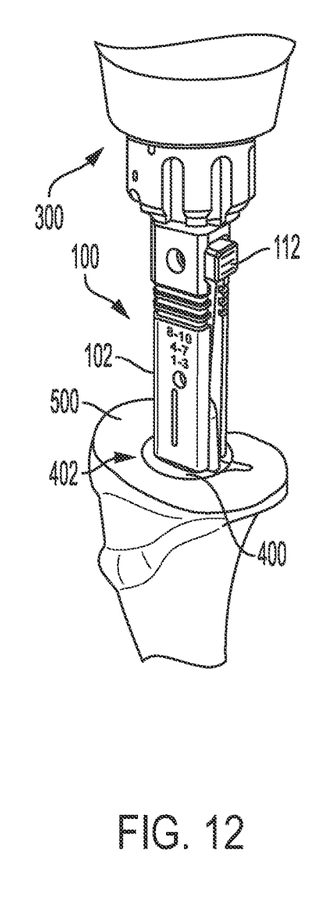
FIG. 12 is a perspective view of the adapter, the surgical impacting tool, and the end effector of FIG. 11 with the end effector positioned in the tibia.
Figure 13:
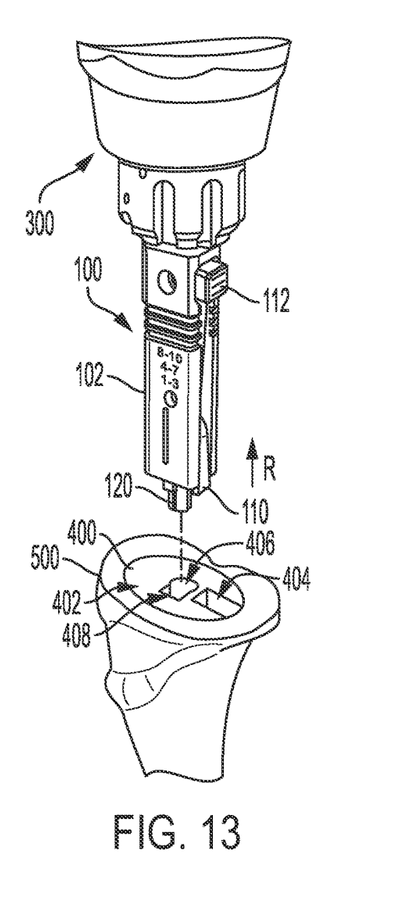
FIG. 13 is a perspective view of the adapter, the surgical impacting tool, and the end effector of FIG. 12 with the adapter and the surgical impacting tool released from the end effector.

FIG. 11 shows the adapter 100 releasably attached to the surgical impacting tool 300 and releasably attached to the end effector 400. FIGS. 11-13 illustrate one embodiment of a method of using the end effector 400 releasably attached to the adapter 100 that is releasably attached to the surgical impacting tool 300.

The surgical impacting tool 300 is actuated to cause the end effector 400 to impact into a tibia 500 of a patient. The surgical impacting tool 300 in this illustrated embodiment is actuated by pulling a trigger 306 on a handpiece 308 of the surgical impacting tool 300 (see FIGS. 9 and 10), but other surgical impacting tools can be actuated in other ways. FIG. 11 shows the end effector 400 impacted into the tibia 500. In an exemplary embodiment, the end effector 400 is impacted into the tibia 500 until a rearward surface 402 of the end effector 400 is at a planned proximal tibial resection surface, as shown in FIG. 12.

If the end effector 400 is unstable in the tibia 500 or does not fill the bone's defect 502, the end effector 400 can be removed from the tibia 500 and the adapter 100 can be released from the end effector 400, e.g., by actuating the button 112. The adapter 100 can then be releasably attached to another end effector for proper fit into the defect 502, for example by attaching a differently sized end effector to the adapter 100. Any number of end effectors can be sequentially releasably attached to the adapter 100 until a desired fit is achieved. In this illustrated embodiment, the end effector 400 desirably fits in the defect 502, as shown in FIG. 12.

With the end effector 400 (or other end effector) desirably fit in the defect 502, the adapter 100 is released from the end effector 400, as shown in FIG. 13. As discussed above, actuating the button 112 of the adapter 100 allows the hook 110 of the adapter 100 to be released from the end effector's notch 404 and the adapter 100 to then be moved horizontally in the rearward direction (arrow R) as a unit with the surgical impacting tool 300, leaving the end effector 400 in the tibia 500 and removing the connector 120 from the end effector's cavity 406.

FIGS. 14-19 illustrate another embodiment of a method of using the adapter 100 and the surgical impacting tool 300. The method of FIGS. 14-19 involves use of another embodiment of an end effector 600, in particular a femoral broach.

To help ensure that a femoral broach such as the end effector 600 is desirably positioned in a femur 602, a broach stop can be used with the adapter 100. The adapter 100 includes a broach stop connector feature 144 configured to releasably attach to a broach stop. The broach stop connector feature 144 in this illustrated embodiment includes a plurality of grooves. The broach stop connector feature 144 in this illustrated embodiment includes three grooves, but another number of grooves is possible, e.g., one, two, four, etc. Having a plurality of grooves allows each of the grooves to correspond to a broach stop size. The adapter 100 can, as in this illustrated embodiment, include a broach stop size guide 146 thereon to indicate which broach stop size(s) corresponds to each of the grooves. In this illustrated embodiment, a forward one of the grooves corresponds to a first size grouping (1-3), a rearward one of the grooves corresponds to a second size grouping (8-10), and an intermediate one of the grooves between the forward and rearward grooves corresponds to a third size grouping (4-7). The broach stop connector feature 144 can have other configurations, such as by including a plurality of protrusions similarly positioned to the plurality of grooves.

Figure 14:
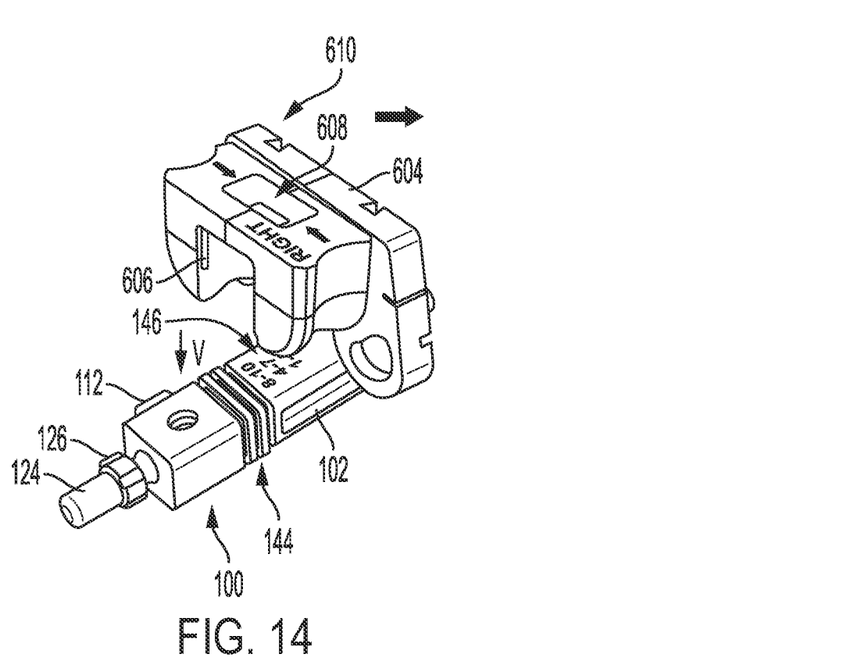
FIG. 14 is a perspective view of the adapter of FIG. 1 and one embodiment of a broach stop.

FIG. 14 illustrates one embodiment of a broach stop 604 configured to releasably attach to the adapter 100 via the broach stop connector feature 144. The broach stop 604 includes an adapter connector feature 606 configured to releasably engage the adapter's broach stop connector feature 144. The broach stop 604 in this illustrated embodiment is in the intermediate size grouping (4-7) so is releasably attached to the intermediate one of the adapter's grooves. The adapter connector feature 606 in this illustrated embodiment includes a protrusion extending along a surface of the broach stop 606 that has a size and shape corresponding to the broach stop connector feature 144 to allow seating of the protrusion in a selected one of the grooves. The protrusion is only partially visible in FIG. 14. The adapter connector feature 606 can have other configurations, such as by including a groove configured to seat in one of a plurality of protrusions extending from an adapter.

The broach stop 604 is a right broach stop in this illustrated embodiment for use in a surgical procedure involving a right femur of a patient. A left broach stop for use in a surgical procedure involving a left femur of a patient can be similarly used with the adapter 100.

In an exemplary embodiment, the adapter 100 is releasably attached to the broach stop 604 by the broach stop 604 moving vertically toward the adapter 100 and/or the adapter 100 moving vertically toward the broach stop 604. FIG. 14 shows the broach stop 604 moving vertically (arrow V) toward the adapter 100 to attach to the adapter 100. The broach stop 604 includes a window 608 formed therein configured to allow visualization therethrough of the one of the sizes of the broach stop size guide 146 that corresponds to the groove to which the broach stop 604 has been attached. The broach stop's correct attachment to the adapter 100 can thus be visually confirmed by a user.

Figure 15:
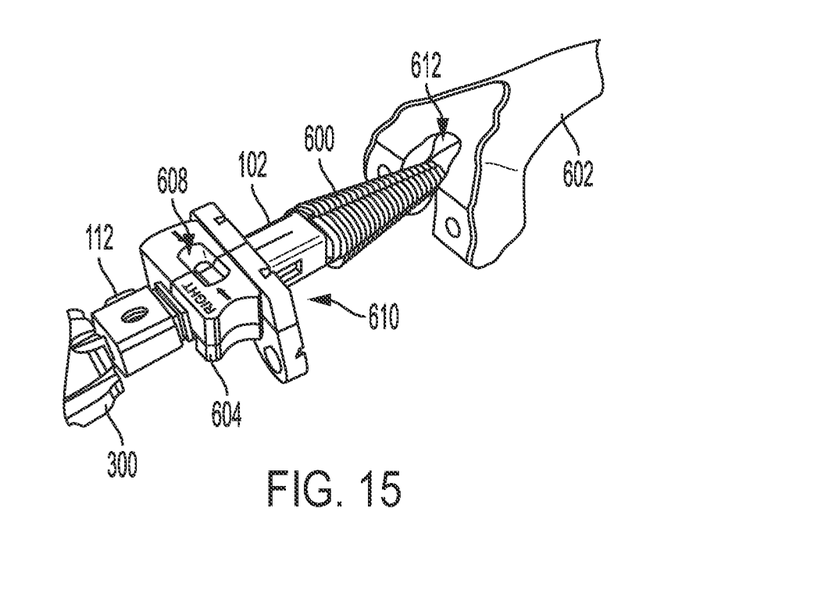
FIG. 15 is a perspective view of the adapter and the broach stop of FIG. 14 coupled together and coupled to the surgical impacting tool of FIG. 9 and to another embodiment of an end effector with a portion of the end effector positioned in a femur.

FIG. 15 shows the broach stop 604 releasably attached to the adapter 100. The intermediate size grouping is visible through the broach stop's window 608. FIG. 15 also shows the end effector 600 releasably attached to the adapter 100. The end effector 600 is attachable to the adapter 100 similar to that discussed above regarding the tibial broach 400. FIG. 15 also shows the surgical impacting tool 300 releasably attached to the adapter 100. As discussed above, the adapter 100 can be releasably attached to the surgical impacting tool 300 before or after the end effector 600 has been releasably attached to the adapter 100. Similarly, the broach stop 604 can be attached to the adapter 100 before or after the end effector 600 has been releasably attached to the adapter 100.

Figure 16:
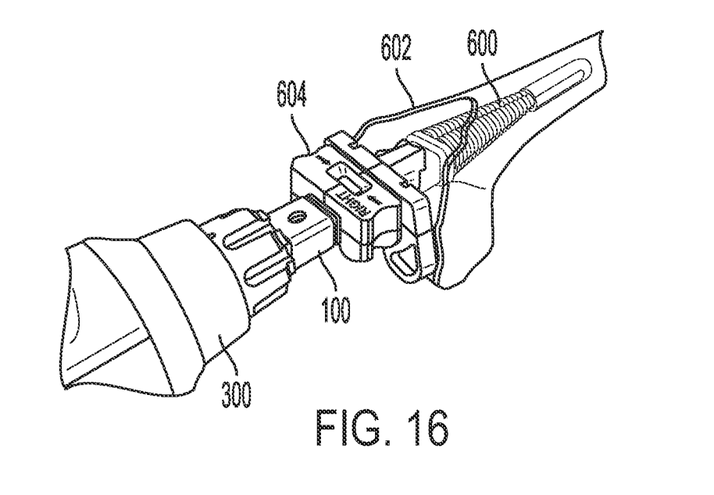
FIG. 16 is a perspective view of the adapter, the broach stop, the end effector, and the surgical impacting tool of FIG. 15 with the end effector positioned in the femur.

The surgical impacting tool 300 is actuated to cause the end effector 600 to impact into the femur 602 of a patient. The surgical impacting tool 300 in this illustrated embodiment is actuated by pulling the trigger 306, as discussed above. FIG. 15 shows the end effector 600 impacted into the femur 602. In an exemplary embodiment, the end effector 600 is impacted into the femur 602 until a forward surface 610 of the broach stop 604 is contacting the femur 602, e.g., a most prominent aspect of a rearward end of the femur 602, as shown in FIG. 16.

If the end effector 600 is unstable in the femur 602 or does not fill the bone's defect 612, the end effector 600 can be removed from the femur 602 and the adapter 100 can be released from the end effector 600, e.g., by actuating the button 112. The adapter 100 can then be releasably attached to another end effector for proper fit into the defect 612, for example by attaching a larger end effector to the adapter 100. Any number of end effectors can be sequentially releasably attached to the adapter 100 until a desired fit is achieved. In this illustrated embodiment, the end effector 600 desirably fits in the defect 612, as shown in FIG. 16.

Figure 17:
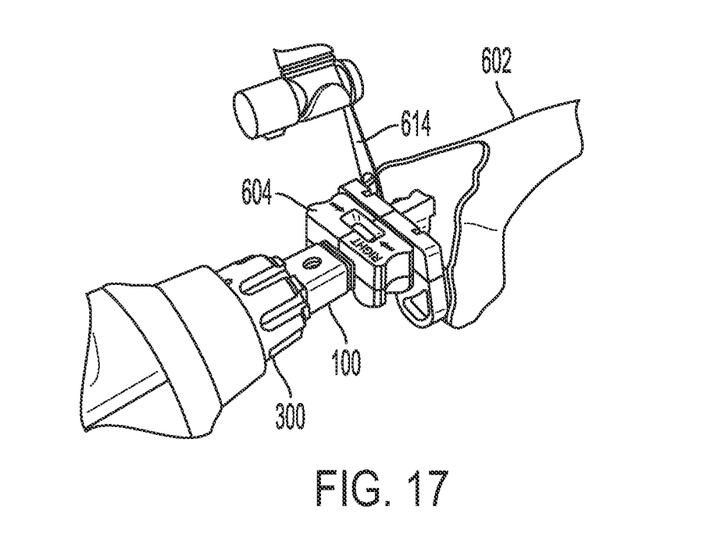
FIG. 17 is a perspective view of the adapter, the broach stop, the end effector, and the surgical impacting tool of FIG. 16 and one embodiment of a broach shim.

With the end effector 600 (or other end effector) desirably fit in the defect 612, a clean-up resection of the femur 602 can be performed, as shown in FIG. 17. A rearward surface of the femur 602 can be resected using the forward surface 610 of the broach stop 604 or a broach shim 614.

Figure 18:
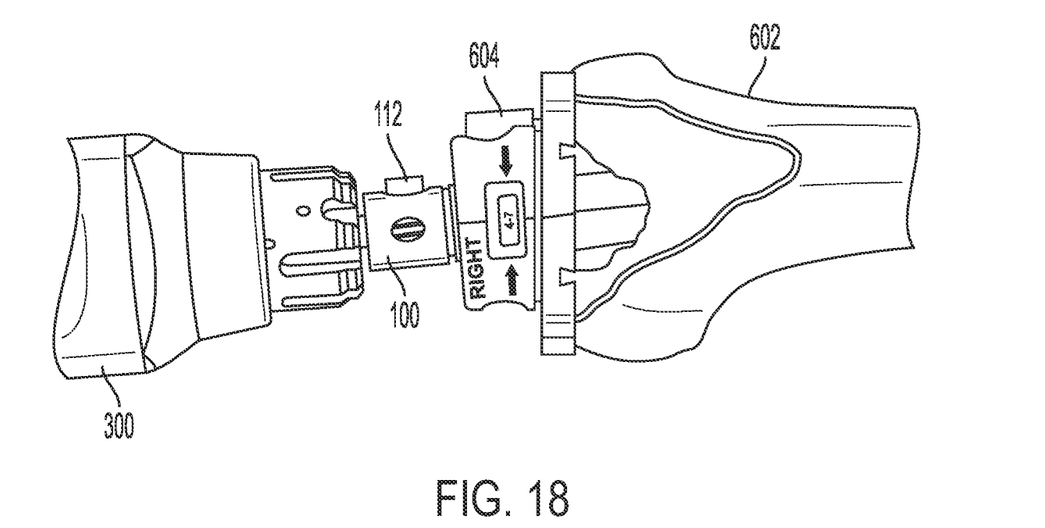
FIG. 18 is a perspective view of the adapter, the broach stop, the end effector, and the surgical impacting tool of FIG. 17 after use of the broach shim.
Figure 19:
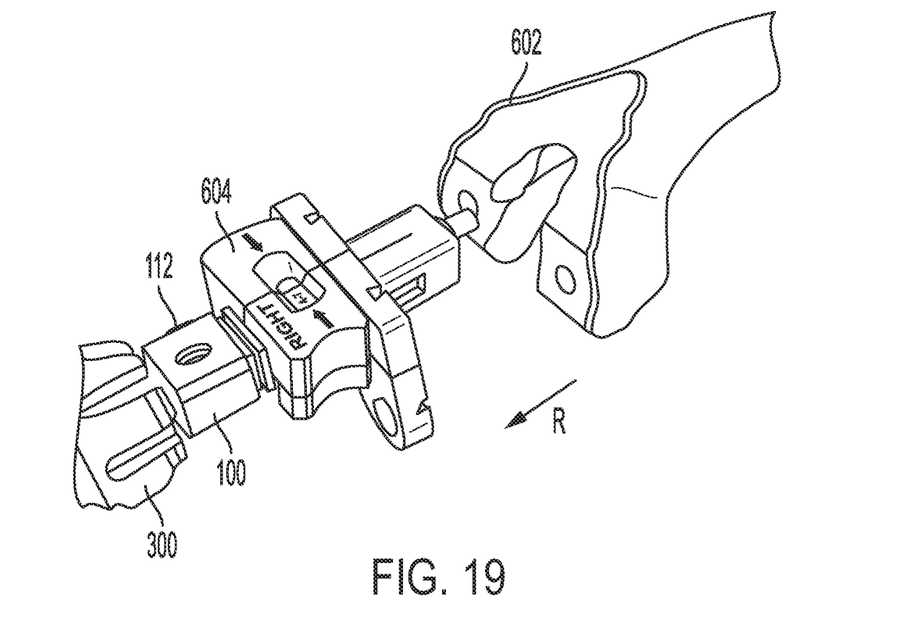
FIG. 19 is a perspective view of the adapter, the broach stop, the surgical impacting tool, and the end effector of FIG. 18 with the adapter, the broach stop, and the surgical impacting tool released from the end effector.

With the end effector 600 (or other end effector) desirably fit in the defect 612, and optional resection having been performed if desired, as shown in FIG. 18, the adapter 100 is released from the end effector 600, as shown in FIG. 19. As discussed above, actuating the button 112 of the adapter 100 allows the hook 110 of the adapter 100 to be released from the end effector's notch and the adapter 100 to then be moved horizontally in the rearward direction (arrow R) as a unit with the surgical impacting tool 300, leaving the end effector 600 in the femur 602 and removing the connector 120 from the end effector's cavity.

One skilled in the art will appreciate further features and advantages of the devices, systems, and methods based on the above-described embodiments. Accordingly, this disclosure is not to be limited by what has been particularly shown and described, except as indicated by the appended claims. All publications and references cited herein are expressly incorporated herein by reference in their entirety.

The present disclosure has been described above by way of example only within the context of the overall disclosure provided herein. It will be appreciated that modifications within the spirit and scope of the claims may be made without departing from the overall scope of the present disclosure.

What is claimed is:

1. A surgical system, comprising:
   an end effector configured to impact bone, a notch being formed in the end effector; and
   an adaptor comprising:
     a rearward end configured to releasably engage an orthopedic impactor, and
     a spring-loaded lever having a hook at a forward end thereof that is configured to be releasably seated in the notch of the end effector, the hook having a sloped forward surface;
   wherein at least one of horizontal movement of the end effector in a rearward direction and horizontal movement of the adapter in a forward direction is configured to cause the adapter and the end effector to come into contact, thereby automatically causing movement of the spring-loaded lever such that the hook releasably seats in the notch;
   the adapter has a top side and a bottom side;
   the lever is located on the bottom side of the adapter;
   the notch is formed in a bottom side of the end effector; and
   with the hook releasably seated in the notch of the end effector, the hook contacts the end effector at only a bottom-facing surface of the notch.

2. The system of claim 1, wherein the adapter further comprises a release mechanism comprising a spring; and
   with the hook releasably seated in the notch, actuation of the release mechanism is configured to cause movement of the hook in a vertical direction such that the hook is released from the notch.

3. The system of claim 1, wherein the hook has a sloped rearward surface that slopes in the forward direction toward a tip of the hook; and
   the sloped forward surface slopes in the rearward direction toward the tip of the hook.

4. The system of claim 1, further comprising one or more additional end effectors, each of the one or more additional end effector having a notch formed therein;
   wherein the hook is configured to releasably seat in one of the notches at a time; and wherein each of the end effector and the one or more additional end effectors is different from one another.

5. The system of claim 1, further comprising the orthopedic impactor;
wherein, with the adapter releasably engaging the orthopedic impactor and with the hook releasably seated in the notch, the orthopedic impactor is configured to drive the end effector to repeatedly impact bone.

6. The system of claim 5, wherein the orthopedic impactor is configured to drive the end effector in a horizontal direction; and
the hook is configured to be released from the notch only by moving in a vertical direction.

7. The system of claim 3, wherein the end effector has a sloped rearward surface that slopes in a forward direction; and
the at least one of horizontal movement of the end effector in the rearward direction and horizontal movement of the adapter in the forward direction is configured to cause the sloped forward surface of the adapter to engage the sloped rearward surface of the end effector and thereby urge the automatic movement of the spring-loaded lever.

8. The system of claim 7, wherein the adapter further comprises a spring that biases the spring-loaded lever; and
the automatic movement of the spring is configured to cause the spring to compress in a vertical direction.

9. The system of claim 5, wherein the orthopedic impactor includes a trigger configured to be manually actuated by a user so as to cause the orthopedic impactor to drive the end effector to repeatedly impact bone.

10. A surgical method, comprising:
moving at least one of the end effector of claim 1 horizontally in the rearward direction and the adapter of claim 1 in the forward direction such that the adapter and the end effector come into contact, thereby causing the movement of the spring-loaded lever of the adapter such that the hook of the lever releasably seats in the notch of the end effector; and
with the adapter coupled to the orthopedic impactor and with the hook releasably seated in the notch, causing the orthopedic impactor to drive the end effector horizontally to impact bone.

11. The method of claim 10, wherein the hook has a sloped rearward surface.

12. The method of claim 10, wherein the hook is only releasable from the notch by moving vertically relative to the end effector.

13. The method of claim 10, further comprising actuating a release mechanism of the adapter, thereby causing the hook to be released from the notch.

14. The method of claim 13, wherein the actuation of the release mechanism causes the hook to move vertically to be released from the notch.

15. The method of claim 13, wherein a spring of the actuator decompresses in response to the hook being seated in the notch; and
the actuation of the release mechanism causes the spring to compress.

16. A surgical system, comprising:
an orthopedic impactor; and
an adaptor comprising:
a rearward end configured to releasably engage the orthopedic impactor,
a body having a cavity formed in a side thereof, the rearward end of the adapter extending rearwardly from the body,
a spring disposed in the body, and
a lever biased by the spring, the lever having a hook at a forward end thereof that is configured to releasably engage an end effector configured to impact bone, the hook having a sloped forward surface, the lever having a button at a rearward end thereof, the button being vertically aligned with the spring and being configured to be actuated to compress the spring in a vertical direction, and the lever being partially seated in the cavity with the hook being located outside of and forward of the cavity;
wherein the adapter defines a first longitudinal axis extending in a horizontal direction between the rearward end of the adapter and a forward end of the adapter;
wherein, with the adapter releasably, engaging the orthopedic, impactor and with the lever releasably engaging the end effector, a trigger of the orthopedic impactor is configured to be actuated so as to drive the end effector to repeatedly impact bone.

17. The system of claim 16, wherein the sloped forward surface slopes at an angle transverse to the first longitudinal axis.

18. The system of claim 16, further comprising the end effector;
wherein the end effector defines a second longitudinal axis extending between a rearward end of the end effector and a forward end of the end effector; and
the hook is configured to be released from the end effector only by moving in a direction that is substantially perpendicular to the first longitudinal axis and the second longitudinal axis.

19. The system of claim 16, wherein the spring is configured to move between an uncompressed configuration, in which the spring biases the lever downward and the hook is configured to releasably engage the end effector, and a compressed configuration, in which the hook is configured to move in a direction substantially perpendicular to the first longitudinal axis to be released from the end effector.

20. The system of claim 16, wherein the hook has a sloped rearward surface that slopes in a forward direction toward a tip of the hook; and
the sloped forward surface slopes in a rearward direction toward the tip of the hook.

21. The system of claim 16, further comprising the end effector;
wherein a notch is formed in the end effector and is configured to releasably seat the hook therein.

22. The system of claim 21, wherein, with the notch releasably seating the hook therein, there is a single point of contact between the hook and the end effector.

23. The system of claim 16, wherein, with the hook releasably engaging the end effector, the compression of the spring is configured to cause movement of the lever such that the hook is released from the end effector.

24. The system of claim 23, further comprising the end effector;
wherein the end effector defines a longitudinal axis extending between a rearward end of the end effector and a forward end of the end effector; and
the movement of the lever is transverse to the longitudinal axis.

25. The system of claim 16, further comprising the end effector;
wherein at least one of horizontal movement of the end effector in a rearward direction and horizontal movement of the adapter in a forward direction is configured to cause the adapter and the end effector to come into contact, thereby automatically causing the spring to compress such that the hook releasably seats in the notch.

26. The system of claim 22, wherein the adapter has a top side and a bottom side;

the lever is located on the bottom side of the adapter;

the notch is formed in a bottom side of the end effector; and with the notch releasably seating the hook therein, the hook contacts the end effector at only a bottom-facing surface of the notch.

\* \* \* \* \*